United States Patent [19]

Moore

[11] Patent Number: 4,638,799
[45] Date of Patent: Jan. 27, 1987

[54] NEEDLE GUIDE APPARATUS FOR DISCOLYSIS PROCEDURES

[76] Inventor: Robert R. Moore, 4010 East Ave., Hayward, Calif. 94545

[21] Appl. No.: 744,392

[22] Filed: Jun. 13, 1985

[51] Int. Cl.⁴ .............................................. A61B 17/00
[52] U.S. Cl. ................................ 128/303 B; 604/116; 604/51
[58] Field of Search ...... 128/303 B, 303.19, DIG. 26; 604/116, 117, 51

[56] References Cited

U.S. PATENT DOCUMENTS

| | | | |
|---|---|---|---|
| 3,941,127 | 3/1976 | Froning | 128/303 B |
| 3,964,480 | 6/1976 | Froning | 128/303 B |
| 4,571,243 | 2/1986 | Froning et al. | 128/303 B |

OTHER PUBLICATIONS

"Surgery" Apr., 1965, vol. 57, No. 4, p. 32.

"The Lancet" Feb. 27, 1960, p. 474.

*Primary Examiner*—Robert Peshock
*Assistant Examiner*—Cary E. Stone
*Attorney, Agent, or Firm*—Bielen and Peterson

[57] ABSTRACT

A needle guide apparatus for accurate insertion of an elongated injection needle into a select intervertebral disc for injection of a lysing agent or dye, particularly during discolysis procedures, the needle guide apparatus includes a mount for connecting the apparatus to a conventional operating table, a vertical and axial adjustment post, an adjustable longitudinal support bar, a connected L-shaped mount structure with a pair of appended needle posts disposed at select angles from the plane of the L-shaped arm, the arm having a connected vertically adjustible indicator post with radioscopically opaque indicators for positioning the apparatus preparatory to insertion of an injection needle into a selected intevertebral disc.

12 Claims, 3 Drawing Figures

NEEDLE GUIDE APPARATUS FOR DISCOLYSIS PROCEDURES

BACKGROUND OF THE INVENTION

This invention relates to a needle guide apparatus to enable accurate insertion of a needle into the spinal area, particularly to aid chemonucleolysis procedures for non-surgical treatment of a herniated invertebral disc.

Certain chemicals have been discovered that dissolve nucleus pulposus material, the gelatinous substance within a vertibral disc. These agents, known generally as lysing agents, when injected into a herniated disc, cause the gelatinous material to dissolve, relieving pressure on nearby spinal nerves. Of the two principal applicable lysing agents, chymopapain and collagenase, chymopapain is used most frequently. Chymopapain is an enzyme derivative from papaya and has been found to dissolve the material forming the nucleus pulposus, without adverse affect on the surrounding annulus fibrosis or thin top and bottom plates of hyaline cartilage. Success from intradiscal injection of chymopapain has provided in many cases, an effective alternative to open back surgery for removal or repair of a herniated disc by a laminectomy procedure.

A major problem with chemonucleolysis procedures however, is the accurate placement of the needle into the nucleus pulposus of the herniated disc. Heretofore, needle placement is in part trial and error, often requiring up to one hour of a treating physcian's time to locate the tip of the needle at the desired point within the disc. In addition to the tedium of the procedure and wasted time, misplacement or repeated perforation can be harmful to the patient. This problem is resolved by the needle guide apparatus devised, which accurately guides and locates the needle at the desired spot in the disc.

The needle guide is primarily used in discolysis procedures, but may be used in other procedures where a substance is injected into a disc or other spinal region.

SUMMARY OF THE INVENTION

The needle guide apparatus of this invention is devised to aid a physician in accurately guiding and locating an injection needle into an invertebral disc, particularly for a chymonucleosis procedure during diagnosis and treatment of a herniated disc. Proper needle placement is important for injection of a dye and subsquent injection of a lysing agent, or in some situations, injection of a combined dye and lysing agent solution.

Chemical excision of herniated nucleus pulposus by injection of a lysing agent, such as chymopapain or collagenase, is an effective alternative to surgery. A most difficult step is the chymonucleosis procedure is insertion and placement of the needle through the annulus fibrosis and into the nucleus pulposus. Because a direct posterior approach will penetrate the spinal cord, and cause possible nerve damage, a more difficult lateral approach is recommended. For discs between the third and forth, and forth and fifth lumbar vertebrae, a 45° angle from the direct posterior axis is preferred, although some surgeons recommend a 55° angle.

The most commonly affected disc is between the fourth and fifth lumbar vertebrae. The second most commonly affected disc, however, is between the fifth lumbar vertebrae and the sacrum, a particularly difficult disc to reach. For this disc a needle positioned at an angle of 45° from the horizontal plane of the sagittal axis must also be positioned at a 30° angle from the cross sectional plane of the spinal column for a diagonal entry into the disc center.

The needle guide apparatus of the preferred embodiments has two individially selectable needle guide posts to properly orient the needle for both the direct 45° angle and the compound 45°/30° angle. The guide posts are removably mountable to an L-shaped support arm which is connected to a bar clamped to a vertical post. The post is clamped to the rail of an operating table.

The vertical post is adjustable in height and pivoted orientation to permit the support bar to be aligned with the patient's spine in the area of the affected disc at an appropriate height. One leg of the L-shaped support arm is adjustably connected to the support bar to move the leg carrying the needle posts toward or away from the patient. Also carried on this leg is an indicator post which supports a radioscopic measuring indicator over the patient for radioscopic positioning of the needle guide apparatus relative to the affected disc.

The 45° angle orientation is preferred to simplify needle placement since the height from the easily determined longitudinal axis of the spine to the needle holder will be equal to the cross distance from the centerline of the disc, as floroscopically determined, to the holder. Therefore, a customary 8 cm. height will require an 8 cm cross distance, which can be provided by positioning a center 8 cm indicator finger over the centerline of the disc. This position is easily achieved by adjustment of the L-shaped support arm toward or away from the patient. The diagonal path line of the needle will then cross the centerline of the disc. The depth of penetration will determine the precise location of the needle end, which can be predetermined to arrive, before, after or at the centerline location.

For the lumbosacral disc, the compound angle is devised to permit a guide needle to penetrate the upper edge of the disc, allowing a smaller injection needle to concentrically feed through the guide needle and curve into the center of the disc, using a double needle technique. The more complicated angle and technique is necessary to avoid the protective iliac crest of the sacrum. Proper centering of the indicators over the center of the disc with a measured entry height of 8 cm will accurately situate the guide needle end on line for the disc axis, with a curve of the injection needle necessary to situate the needle end centrally between the hyaline cartilage plates.

Apparatus devised with needle post angles differing from the preferred, may require different height and cross distance measurements for geometric determination of the proper needle path.

Once the needle guide apparatus is properly positioned and checked, the inserted needle will be guided to the proper location for injection. Final positioning is determined through feel and subsequent x-ray imaging.

DETAILED DESCRIPTION OF THE PREFERRED EMBODIMENT

Figure 1:
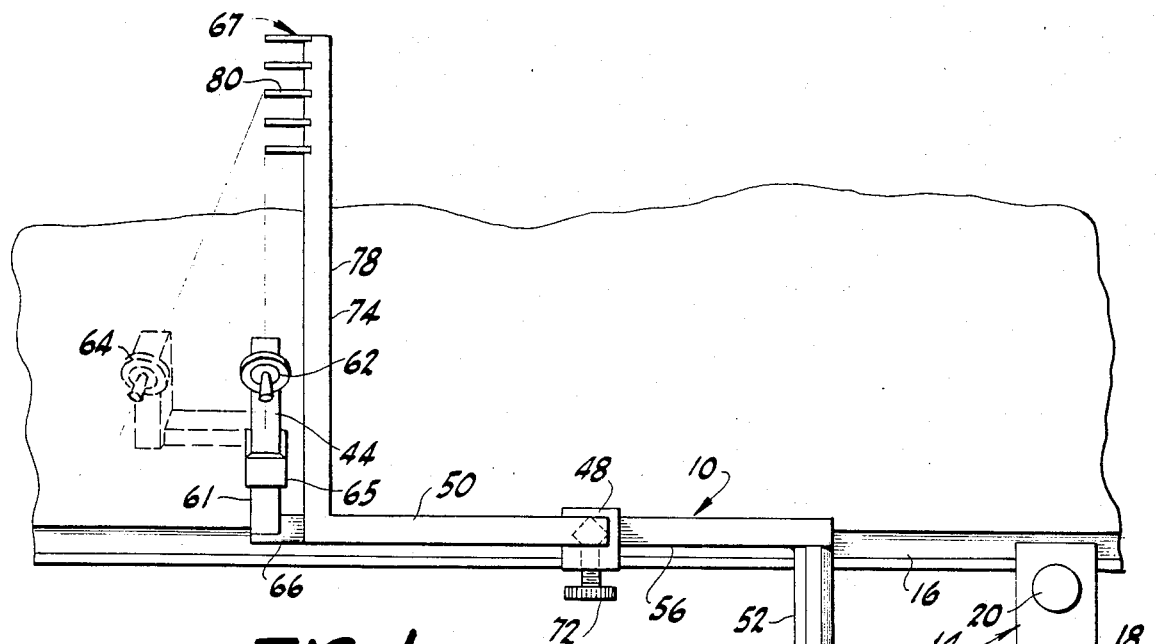
FIG. 1 is a top view of the needle guide apparatus mounted to a conventional operating table.
Figure 2:
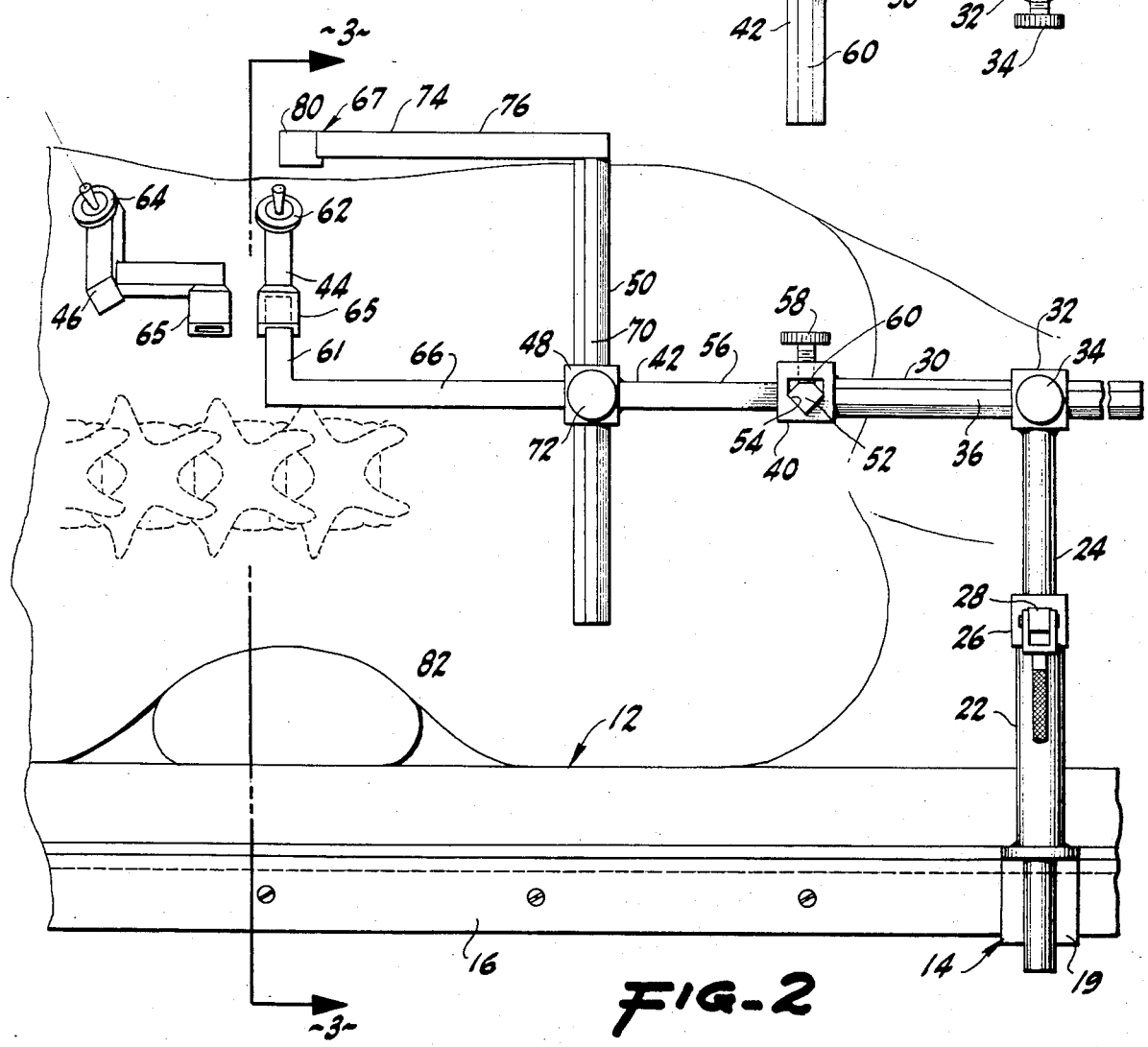
FIG. 2 is a side elevational view of the guide apparatus of FIG. 1, with reference to a patient in a lateral decubital position on the table.
Figure 3:
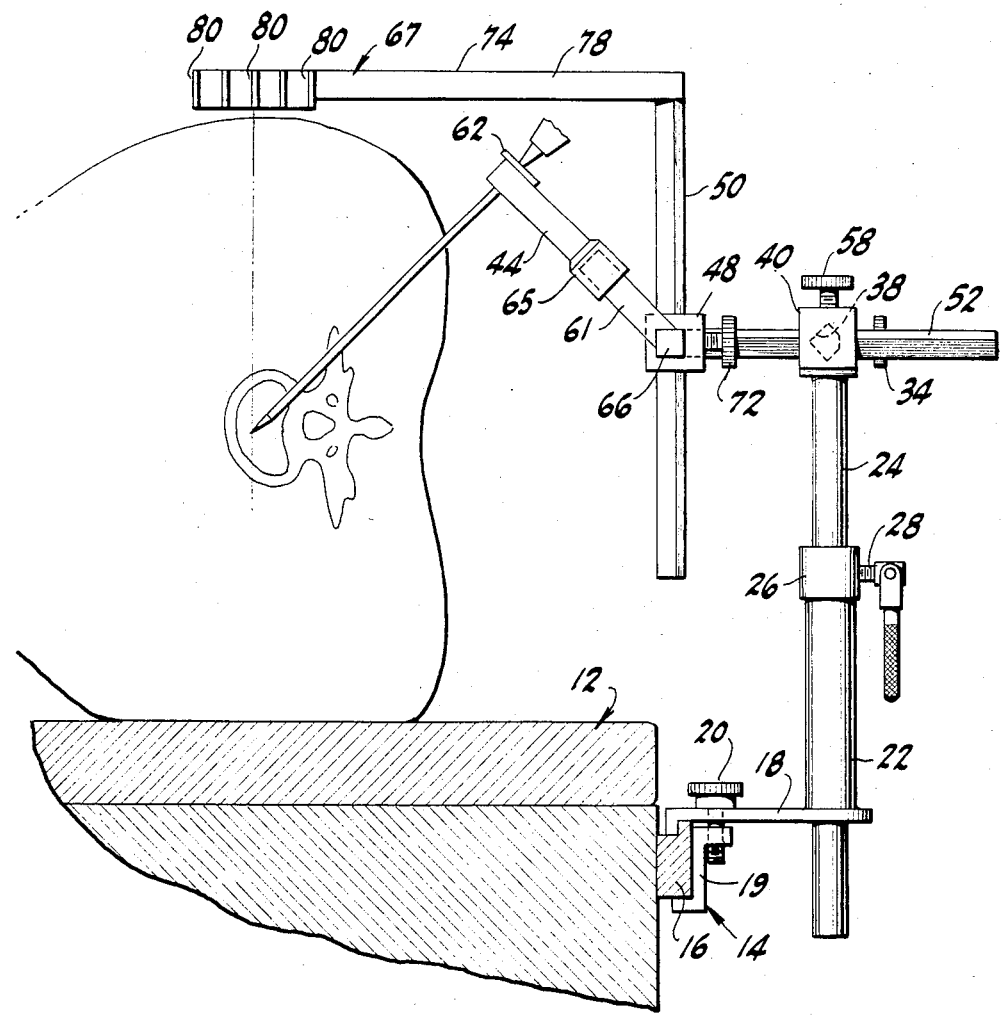
FIG. 3 is a cross sectional view taken on the lines 3—3 in FIG. 2.

Referring to the drawing, the needle guide apparatus of this invention is designated generally by the reference numeral 10. The needle guide apparatus 10 as shown in FIGS. 1-3 is connected to a conventional operating table 12 by a rail clamp unit 14, which engages side rail 16 along the edge of the table. The clamp unit 14 has a top plate 18 contacting the top and back of the rail, and a clamping plate 19 contacting the front and underside of the rail. A clamping screw 20 in the top plate threadably engages the clamping plate to secure the top plate against the rail on tightening of the clamping screw 20. Other conventional means may be utilized to secure the needle guide apparatus to a rail equiped operating table, or to an examining or x-ray table used for a chemo-nucleolysis procedure or other procedure where accurate guidance of a needle into a patient is desired.

The needle guide apparatus may be used, for example for accurate needle placement for dye injections or fluid taps in spinal diagnosis procedures, in procedures prepatory to a laminectomy or other procedures demanding accurate needle placement in the spinal area. Because the needle guide apparatus is adjusted relative to the sagittal axis along the centerline of the patient's disc, the apparatus is useable for patients of different size without individual adjustment except for aligments to the spinal reference axis.

The needle guide apparatus includes a post socket 22 fixed to the top plate 18 of the clamp unit 14. A vertical support post 24 is slidably and pivotally engaged with the post socket 22. The socket 22 has a top collar 26 with a crank operated stop screw 28 to fix the support post at the height and axial orientation desired The support post 24 retains a horizontal support bar 30 in a screw clamp 32 at the distal upper end of the post 24. The screw clamp 32, includes a turn screw 34 which contacts a flat side surface 36 of the slidable support bar 30. Tightening the turn screw 34 fixes the support bar at the desired longitudinal position along side the patient, shown in phantom in FIGS. 2 and 3. The support bar is oriented with a sidewardly disposed corner edge that wedges the bar firmly in the conforming slot 38 in the screw clamp to provide an accurate seating on tightening the turn screw.

The longitudinal support bar 30 has a screw clamp 40 at its distal end which engages an L-shaped mount arm 42. Selectively mountable on the L-shaped arm 42 are either of needle guide posts 44 and 46 and a screw clamp 48 for retaining a vertically adjustable indicator post 50. The L-shaped mount arm 42 has a first leg 52 that is slidably connected to a conforming slot 54 in the screw clamp 40 to permit a horizontal second leg 56, on which the needle posts and the indicator post are mounted to move toward or away from the patient. The selected position is secured by tightening a turn screw 58 on the screw clamp 40 which contacts a flat top surface 60 on the first leg 52 in a manner similar to the support post clamp 32.

The two needle guide posts 44 and 46 are mounted at a 45° from a horizontal plane, and are disposed in an upward direction toward the patient. Guide post 46 is shown in dotted line in FIG. 1, and exploded from the terminal post 61 of the angled terminal end 61 of the second leg 56 of the mount arm 42.

Needle guide sleeves 62 and 64 are installed in the end of the guide posts perpendicular to the posts, directing inserted needles in a downward lateral direction. The guide sleeve 64 in the post 46 at the distal end of the second arm is further oriented at a 30° caudad angle for needle placement in the lumbosacral disc. The needle guides sleeves 62 and 64 provide a linear guide at a predefined entry angle for an inserted needle.

The posts 44 and 46 have a square end socket 65 for removable mounting of the posts on the end 61 of the second leg 56 of the mount arm. The posts 44 are shown in FIG. 1 with their socket stems 66 superimposed to illustrate the relative installed position of the two posts. The compound angle of the outer post requires an additional displacement to locate the tip of an inserted needle in the appropriate disc as aligned with radioscopic indicator means 67. Alternately, the posts can be fixed in the positions shown, or oppositely mounted on a single stem which can be rotated to position the selected post in the operable position.

Approximately midpoint on the second leg 56 is a vertically oriented screw clamp 48 to slidably engage a vertical indication post 50. The indicator post 50 has a similar wedge cross section with a flat clamping surface 70 which is contacted by a turn screw 72 on the screw clamp to lock the indicator post 50 at a desired position. The indicator post 50 has a L-shaped mount arm 74 at its distal upper end with a longitudinal leg 76 and a cross leg 78 on which is mounted the indicator means 67. The indicator means comprises radioscopically opaque indicator fingers 80 marking the 4, 6, 8, 10 and 12 cm point from the needle guide sleeves. The indicator fingers 80 are positioned over and across the patient such that on a discography, the indicators will appear to mark points across the sagittal axis through the centerline of the discs. By adjustment of the needle guide the central indicator can be aligned with the centerline of the affected disc with the end of the indicator positioned over the midpoint or center of the disc to orient the connected needle guide sleeve for needle penetration of the affected disc.

As shown in FIG. 2 a patient rests on the table in a lateral decubital position with his posterior side facing the apparatus. A support cushion 82 is placed under the recumbant flank to adjust the spine on a linear sagittal axis. Since the patient's spine may not be aligned with the side rail 16 of the table 12, the vertical support post 24 is pivotally adjusted in the post socket 22 to align the first leg 52 of the mount arm 42 with the sagittal axis. The height of the support post is adjusted to horizontally align a select needle guide sleeve with a marking on the patient, 8 cm above the sagittal centerline axis. The post is secured by tightening the crank operated stop screw 28. The indicator post 68 is adjusted in height in the screw clamp 66 to orient the indicators close to the patient to maximize image clarity on discography. The fore and aft position of the select needle post is adjusted by movement of the horizontal support bar 30 in the screw clamp 32 to position the post at the affected disc. The position should be checked for final adjustment on discography where the indicator fingers are superimposed on the disc prior to the needle insertion.

The location of the guide transverse to the sagittal axis can be approximately and finally positioned on discography, aligning end edge of the 8 cm center finger with the centerline of the disc. If the alignment edge is not in the desired position, both the anteriorposterior and the superior-inferior discrepancies can be measured off the original image. The proper adjustment can then be made using screw clamp 32 for support bar 30 and clamp unit 14 for post 24. A second image is then taken to see that the corrections are accurate.

If another position indicator (i.e. no. 6 or no. 10) is above the disc space, then only the needle post support bar 30 need be raised or lowered, with clamp unit 14 for post 24 to the corresponding level above the spinous process (i.e. 6 cm or 10 cm).

The same procedure is used for both needle guide posts 44 and 46. Penetration of the needle should be closely monitored by discography to locate the needle tip at the desired point in the affected disc before injection. In this manner the needle guide apparatus permits accurate penetration of the needle at the desired angular orientation to situate the needle tip safetly into the affected disc.

The angular orientation of the needle guide posts represents the current practice. It is understood that the angular orientations of the removeable posts can easily be altered on manufacture to represent the best current practice as the surgical procedure becomes refined.

While in the foregoing embodiments of the present invention have been set forth in considerable detail for the purpose of making a complete disclosure of the invention, it may be apparent to those of skill in the art that numerous changes may be made in such detail without departing from the spirit and principles of the invention.

What is claimed is:

1. A needle guide apparatus for directing an injection needle into a spinal disc of a patient on a conventional operating table having a side rail with the patient having a sagittal this longitudinally oriented to the table comprising:
   (a) mounting means for connecting the apparatus to the table in a posterior location to a patient lying in a lateral decubital position on the table;
   (b) needle guide means for guiding the injection needle on a select penetration angle into the lateral posterior of the patient;
   (c) adjustable support structure supporting said needle guide means and interconnecting said guide means with said mounting means said support structure having adjustable means for locating said needle guide means at a predetermined location for accurate guide of a needle into a select spinal disc wherein said adjustable support structure comprises at least one vertical member with adjustment means for adjusting the height of the needle guide means, at least one horizontal member disposed parallel to the sagittal axis of the patient, said horizontal member cooperating with connected adjustment means for adjusting the fore and aft position of said needle guide means parallel to the sagittal axis of the patient, and at least one transverse member disposed transverse of the sagittal axis of the patient said transverse member cooperating with connected adjustment means for adjusting the cross position of said needle guide means transvrse to the sagittal axis of the patient;
   (d) indicator means connected to said support structure for indicating the relative position of said guide means relative to the select disc.

2. The needle guide apparatus of claim 1 wherein said needle guide means comprises a needle guide sleeve mounted on said support structure at a predetermined guide angle.

3. The needle guide apparatus of claim 1 wherein said mounting means comprises a clamp unit adapted to connect the guide apparatus to the side rail of the operating table.

4. The needle guide apparatus of claim 1 wherein said adjustment means of said vertical member includes pivotal orienting means for adjusting the alignment of said horizontal member parallel to the sagittal axis of the patient.

5. The needle guide apparatus of claim 4 wherein said vertical member comprises a post socket and post engaged in said socket and said adjustment means includes a clamp unit on said socket which engages said post retaining said post in a select vertical and axial position.

6. The needle guide apparatus of claim 5 wherein said post has a distal end with a clamp, said horizontal member comprising a support bar engaged with said clamp.

7. The needle guide apparatus of claim 6 wherein said horizontal support bar has a distal end with a clamp, said transverse member comprising a L-shaped arm with a transverse leg engaged with said clamp of said support bar.

8. The needle guide apparatus of claim 7 wherein said L-shaped arm has a second horizontal leg perpendicular to said first leg on which is mounted a post for support of said needle guide means.

9. The needle guide apparatus of claim 1 wherein said needle guide means orients a needle at a 45° downward angle from a horizontal plane.

10. The needle guide apparatus of claim 1 wherein said needle guide means orients a needle at a 45° downward angle from a horizontal plane and a 30° caudad angle.

11. The needle guide apparatus of claim 1 wherein said indicator means comprises at least one radioscopically opaque indicator positioned over the patient.

12. The needle guide apparatus of claim 11 wherein said indicator means has a fixed position relative to said needle guide means and is adjustable therewith.

* * * * *